United States Patent
Al-Ali et al.

(10) Patent No.: US 11,937,949 B2
(45) Date of Patent: Mar. 26, 2024

(54) PHYSIOLOGICAL PARAMETER SYSTEM

(71) Applicant: Masimo Corporation, Irvine, CA (US)

(72) Inventors: Ammar Al-Ali, San Juan Capistrano, CA (US); John Graybeal, Grantville, PA (US); Massi Joe E. Kiani, Laguna Niguel, CA (US); Michael Petterson, Dana Point, CA (US)

(73) Assignee: Masimo Corporation, Irvine, CA (US)

( * ) Notice: Subject to any disclaimer, the term of this patent is extended or adjusted under 35 U.S.C. 154(b) by 167 days.

(21) Appl. No.: 17/466,287

(22) Filed: Sep. 3, 2021

(65) Prior Publication Data

US 2022/0054093 A1 Feb. 24, 2022

Related U.S. Application Data

(60) Division of application No. 16/159,278, filed on Oct. 12, 2018, now Pat. No. 11,109,814, which is a continuation of application No. 14/275,525, filed on May 12, 2014, now Pat. No. 10,098,591, which is a division of application No. 12/188,154, filed on Aug. 7, 2008, now Pat. No. 8,721,542, which is a
(Continued)

(51) Int. Cl.
*A61B 5/00* (2006.01)
*A61B 5/1455* (2006.01)
*A61B 5/083* (2006.01)

(52) U.S. Cl.
CPC ........ *A61B 5/7275* (2013.01); *A61B 5/14551* (2013.01); *A61B 5/7221* (2013.01); *A61B 5/746* (2013.01); *A61B 5/0836* (2013.01); *A61B 2560/0276* (2013.01)

(58) Field of Classification Search
None
See application file for complete search history.

(56) References Cited

U.S. PATENT DOCUMENTS 4,453,218 A  6/1984 Sperinde et al.
4,960,128 A  10/1990 Gordon et al.
(Continued)

FOREIGN PATENT DOCUMENTS

WO  WO 98/010699  3/1998
WO  WO 03/053503  7/2003
(Continued)

OTHER PUBLICATIONS

Bloom, Marc J., "Techniques to Identify Clinical Contexts During Automated Data Analysis", nternational Journal of Clinical Monitoring and Computing Netherlands, Feb. 1993, vol. 10, No. 1, pp. 17-22.
(Continued)

*Primary Examiner* — Shirley X Jian
(74) *Attorney, Agent, or Firm* — Knobbe, Martens, Olson & Bear, LLP

(57) ABSTRACT

A physiological parameter system has one or more parameter inputs responsive to one or more physiological sensors. The physiological parameter system may also have quality indicators relating to confidence in the parameter inputs. A processor is adapted to combine the parameter inputs, quality indicators and predetermined limits for the parameters inputs and quality indicators so as to generate alarm outputs or control outputs or both.

14 Claims, 8 Drawing Sheets

Related U.S. Application Data continuation of application No. 11/075,389, filed on Mar. 8, 2005, now Pat. No. 7,415,297.

(60) Provisional application No. 60/600,640, filed on Aug. 11, 2004, provisional application No. 60/551,165, filed on Mar. 8, 2004.

(56) References Cited

U.S. PATENT DOCUMENTS

| | | |
|---|---|---|
| 4,964,408 A | 10/1990 | Hink et al. |
| 5,123,420 A | 6/1992 | Paret |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,895,371 A | 4/1999 | Levitas et al. |
| 5,919,134 A | 7/1999 | Diab |
| 5,957,885 A * | 9/1999 | Bollish ............ A61M 5/1723 604/67 |
| 5,987,343 A | 11/1999 | Kinast |
| 5,997,343 A | 12/1999 | Mills et al. |
| 6,002,952 A | 12/1999 | Diab et al. |
| 6,010,483 A | 1/2000 | Spencer |
| 6,010,937 A | 1/2000 | Karam et al. |
| 6,027,452 A | 2/2000 | Flaherty et al. |
| 6,040,578 A | 3/2000 | Malin et al. |
| 6,053,887 A | 4/2000 | Levitas et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,178,343 B1 | 1/2001 | Bindszus et al. |
| 6,184,521 B1 | 2/2001 | Coffin, IV et al. |
| 6,215,403 B1 | 4/2001 | Chan et al. |
| 6,232,609 B1 | 5/2001 | Snyder et al. |
| 6,241,683 B1 | 6/2001 | Macklem et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,337,629 B1 | 1/2002 | Bader |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,449,501 B1 | 9/2002 | Reuss |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,654,632 B2 | 11/2003 | Lange et al. |
| 6,658,276 B2 | 12/2003 | Kiani et al. |
| 6,661,161 B1 | 12/2003 | Lanzo et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,751,499 B2 | 6/2004 | Lange et al. |
| 6,754,516 B2 | 6/2004 | Mannheimer |
| 6,757,558 B2 | 6/2004 | Lange et al. |
| 6,760,607 B2 | 7/2004 | Al-Ali |
| 6,768,920 B2 | 7/2004 | Lange et al. |
| 6,788,965 B2 | 9/2004 | Ruchti et al. |
| 6,811,538 B2 | 11/2004 | Westbrook et al. |
| 6,816,241 B2 | 11/2004 | Grubisic |
| 6,822,564 B2 | 11/2004 | Al-Ali |
| 6,826,426 B2 | 11/2004 | Lange et al. |
| 6,847,899 B2 | 1/2005 | Allgeyer |
| 6,850,787 B2 | 2/2005 | Weber et al. |
| 6,850,788 B2 | 2/2005 | Al-Ali |
| 6,876,931 B2 | 4/2005 | Lorenz et al. |
| 6,920,345 B2 | 7/2005 | Al-Ali et al. |
| 6,934,570 B2 | 8/2005 | Kiani et al. |
| 6,943,348 B1 | 9/2005 | Coffin, IV |
| 6,956,649 B2 | 10/2005 | Acosta et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| 7,081,095 B2 | 7/2006 | Lynn et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,225,006 B2 | 5/2007 | Al-Ali et al. |
| RE39,672 E | 6/2007 | Shehada et al. |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,316,231 B2 | 1/2008 | Hickle |

(56) References Cited

U.S. PATENT DOCUMENTS

| | | |
|---|---|---|
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,377,794 B2 | 5/2008 | Al-Ali et al. |
| 7,387,608 B2 | 6/2008 | Dunlop et al. |
| 7,395,158 B2 | 7/2008 | Monfre et al. |
| 7,407,485 B2 | 8/2008 | Huiku |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,539,537 B2 | 5/2009 | Hickle |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,758,503 B2 * | 7/2010 | Lynn .................. A61B 5/4818 600/300 |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,802,571 B2 | 9/2010 | Tehrani |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,401,602 B2 | 3/2013 | Kiani |
| 8,401,607 B2 | 3/2013 | Mannheimer |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 * | 4/2013 | Al-Ali .................. A61B 5/02416 600/323 |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,932,227 B2 | 1/2015 | Lynn |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |

(56) References Cited

U.S. PATENT DOCUMENTS

| | | |
|---|---|---|
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,109,814 B2 | 9/2021 | Al-Ali et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |

(56) References Cited

U.S. PATENT DOCUMENTS

| | | |
|---|---|---|
| D950,599 S | 5/2022 | Ahmed |
| D950,738 S | 5/2022 | Al-Ali et al. |
| D957,648 S | 7/2022 | Al-Ali |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0107434 A1 | 8/2002 | Lange et al. |
| 2002/0111754 A1 | 8/2002 | Lange et al. |
| 2002/0133080 A1 | 9/2002 | Apruzzese et al. |
| 2002/0190863 A1 | 12/2002 | Lynn |
| 2003/0000522 A1 | 1/2003 | Lynn et al. |
| 2003/0013975 A1 | 1/2003 | Kiani |
| 2003/0018243 A1 | 1/2003 | Gerhardt et al. |
| 2003/0106553 A1 | 6/2003 | Vanderveen |
| 2003/0144582 A1 | 7/2003 | Cohen et al. |
| 2003/0145854 A1* | 8/2003 | Hickle ............. A61M 16/0093 128/204.23 |
| 2003/0156288 A1 | 8/2003 | Barnum et al. |
| 2003/0158466 A1* | 8/2003 | Lynn ................. A61B 5/00 600/300 |
| 2003/0212312 A1 | 11/2003 | Coffin, IV et al. |
| 2004/0106163 A1 | 6/2004 | Workman, Jr. et al. |
| 2004/0111014 A1 | 6/2004 | Hickle |
| 2004/0127792 A1 | 7/2004 | Siejko et al. |
| 2004/0193068 A1 | 9/2004 | Burton et al. |
| 2005/0055276 A1 | 3/2005 | Kiani et al. |
| 2005/0109340 A1 | 5/2005 | Tehrani |
| 2005/0177096 A1 | 8/2005 | Bollish et al. |
| 2005/0203352 A1 | 9/2005 | Al-Ali et al. |
| 2005/0234317 A1 | 10/2005 | Kiani |
| 2006/0073719 A1 | 4/2006 | Kiani |
| 2006/0189871 A1 | 8/2006 | Al-Ali et al. |
| 2006/0276695 A9* | 12/2006 | Lynn ....................... G16H 50/70 600/300 |
| 2007/0073116 A1 | 3/2007 | Kiani et al. |
| 2007/0129647 A1 | 6/2007 | Lynn |
| 2007/0180140 A1 | 8/2007 | Welch et al. |
| 2007/0191697 A1 | 8/2007 | Lynn et al. |
| 2007/0244377 A1 | 10/2007 | Cozad et al. |
| 2007/0299389 A1 | 12/2007 | Halbert et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2008/0300471 A1 | 12/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0296672 A1 | 11/2013 | O'Neil et al. |
| 2013/0345921 A1 | 12/2013 | Al-Ali et al. |
| 2014/0081100 A1 | 3/2014 | Muhsin et al. |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0137988 A1 | 5/2015 | Gravenstein et al. |
| 2016/0196388 A1 | 7/2016 | Lamego |
| 2016/0283665 A1 | 9/2016 | Sampath et al. |
| 2016/0367173 A1 | 12/2016 | Dalvi et al. |
| 2017/0024748 A1 | 1/2017 | Haider |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0125430 A1 | 5/2018 | Al-Ali et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2019/0117070 A1 | 4/2019 | Muhsin et al. |
| 2019/0239787 A1 | 8/2019 | Pauley et al. |
| 2019/0320906 A1 | 10/2019 | Olsen |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |

(56) References Cited

U.S. PATENT DOCUMENTS

| | | |
|---|---|---|
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |

FOREIGN PATENT DOCUMENTS

| | | |
|---|---|---|
| WO | WO 2005/056087 | 6/2005 |
| WO | WO 2005/087097 | 9/2005 |

OTHER PUBLICATIONS

Horn, Werner, et al. "Effective Data Validation of High-Frequency Data: Time-Point-, Time-Interval-, and Trend-Based Methods", Computers in Biology and Medicine, Sep. 1997, vol. 27, No. 5, pp. 389-409.

International Search Report and Written Opinion received in PCT Application No. PCT/US2005/007580, dated Aug. 23, 2005.

* cited by examiner

PHYSIOLOGICAL PARAMETER SYSTEM

CROSS-REFERENCE TO RELATED APPLICATIONS

This application is a divisional of U.S. patent application Ser. No. 16/159,278, titled Physiological Parameter System, filed Oct. 12, 2018, which is a continuation of U.S. patent application Ser. No. 14/275,525 (now U.S. Pat. No. 10,098,591), titled Physiological Parameter System, filed May 12, 2014, which is a divisional of U.S. patent application Ser. No. 12/188,154 (now U.S. Pat. No. 8,721,542), titled Physiological Parameter System, filed Aug. 7, 2008, which is a continuation of U.S. patent application Ser. No. 11/075,389 (now U.S. Pat. No. 7,415,297), titled Physiological Parameter System, filed Mar. 8, 2005, which relates to and claims the benefit of U.S. Provisional Applications No. 60/551,165, titled Combined Physiological Parameter Monitor, filed Mar. 8, 2004 and No. 60/600,640, titled Physiological Parameter Controller, filed Aug. 11, 2004. Each of the foregoing applications are incorporated by reference herein.

BACKGROUND OF THE INVENTION

Pulse oximetry is a widely accepted noninvasive procedure for measuring the oxygen saturation level of arterial blood, an indicator of a person's oxygen supply. Early detection of a low blood oxygen level is critical in the medical field, for example in critical care and surgical applications, because an insufficient supply of oxygen can result in brain damage and death in a matter of minutes. A typical pulse oximetry system utilizes a sensor applied to a patient's finger. The sensor has an emitter configured with both red and infrared LEDs that project light through the finger to a detector so as to determine the ratio of oxygenated and deoxygenated hemoglobin light absorption. In particular, the detector generates first and second intensity signals responsive to the red and IR wavelengths emitted by the LEDs after absorption by constituents of pulsatile blood flowing within a fleshy medium, such as a finger tip. A pulse oximetry sensor is described in U.S. Pat. No. 6,088,607 titled Low Noise Optical Probe, which is assigned to Masimo Corporation, Irvine, CA and incorporated by reference herein.

Capnography comprises the continuous analysis and recording of carbon dioxide concentrations in the respiratory gases of patients. The device used to measure the $CO_2$ concentrations is referred to as a capnometer. $CO_2$ monitoring can be performed on both intubated and non-intubated patients. With non-intubated patients, a nasal cannula is used. Capnography helps to identify situations that can lead to hypoxia if uncorrected. Moreover, it also helps in the swift differential diagnosis of hypoxia before hypoxia can lead to irreversible brain damage. Pulse oximetry is a direct monitor of the oxygenation status of a patient. Capnography, on the other hand, is an indirect monitor that helps in the differential diagnosis of hypoxia so as to enable remedial measures to be taken expeditiously before hypoxia results in an irreversible brain damage.

SUMMARY OF THE INVENTION

Multiple physiological parameters, combined, provide a more powerful patient condition assessment tool than when any physiological parameter is used by itself. For example, a combination of parameters can provide greater confidence if an alarm condition is occurring. More importantly, such a combination can be used to give an early warning of a slowly deteriorating patient condition as compared to any single parameter threshold, which may not indicate such a condition for many minutes. Conditions such as hypovolemia, hypotension, and airway obstruction may develop slowly over time. A physiological parameter system that combines multiple parameters so as to provide an early warning could have a major effect on the morbidity and mortality outcome in such cases.

Further, a greater emphasis has been put on decreasing the pain level of patients on the ward. Accordingly, patients are often given an IV setup that enables the patient to increase the level of analgesia at will. In certain situations, however, the patient's input must be ignored so as to avoid over medication. Complications from over sedation may include hypotension, tachycardia, bradycardia, hypoventilation and apnea. A physiological parameter system that uses pulse oximetry monitoring of $SpO_2$ and pulse rate in conjunction with patient controlled analgesia (PCA) can aid in patient safety. Utilization of conventional pulse oximetry in conjunction with PCA, however, can result in the patient being erroneously denied pain medication. Conventional monitors are susceptible to patient motion, which is likely to increase with rising pain. Further, conventional monitors do not provide an indication of output reliability.

Advanced pulse oximetry is motion tolerant and also provides one or more indications of signal quality of data confidence. These indicators can be used as arbitrators in decision algorithms for adjusting the PCA administration and sedation monitoring. Further, advanced pulse oximetry can provide parameters in addition to oxygen saturation and pulse rate, such as perfusion index (PI). For example hypotension can be assessed by changes in PI, which may be associated with changes in pulse rate. Motion tolerant pulse oximetry is described in U.S. Pat. No. 6,699,194 titled Signal Processing Apparatus and Method; signal quality and data confidence indicators are described in U.S. Pat. No. 6,684,090 titled Pulse Oximetry Data Confidence Indicator, both of which are assigned to Masimo Corporation, Irvine, CA and incorporated by reference herein.

One aspect of a physiological parameter system in a first parameter input responsive to a first physiological sensor and a second parameter input responsive to a second physiological sensor. A processor is adapted to combine the parameters and predetermined limits for the parameters so as to generate an alarm output.

Another aspect of a physiological parameter system is a parameter input responsive to a physiological sensor and a quality indicator input relating to confidence in the parameter input. A processor is adapted to combine the parameter input, the quality indicator input and predetermined limits for the parameter input and the quality indicator input so as to generate a control output.

A physiological parameter method comprises the steps of inputting a parameter responsive to a physiological sensor and inputting a quality indicator related to data confidence for the parameter. A control signal is output from the combination of the parameter and the quality indicator. The control signal is adapted to affect the operation of a medical-related device.

DETAILED DESCRIPTION OF THE PREFERRED EMBODIMENTS

Figure 1:
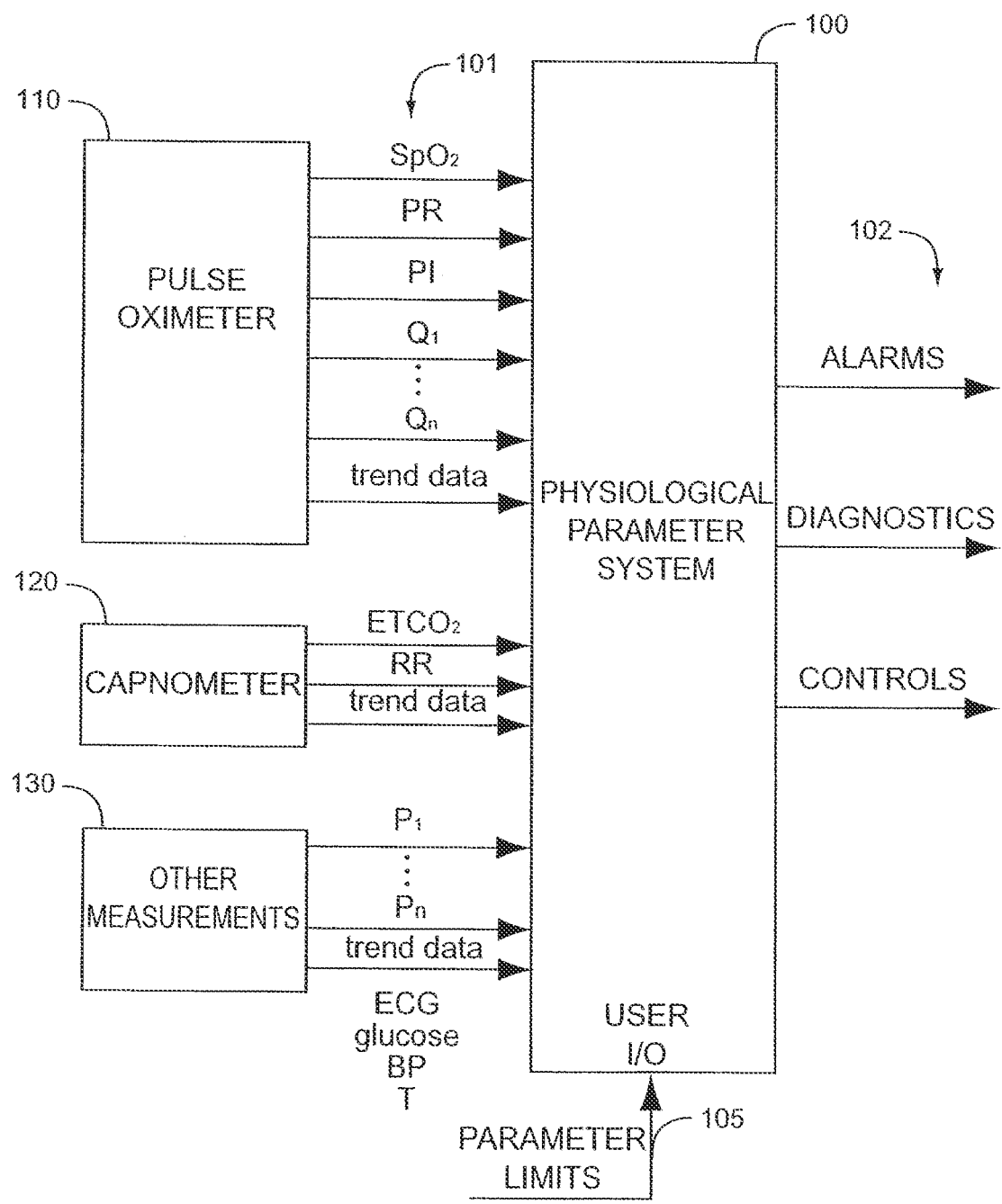
FIG. 1 is a general block diagram of a physiological parameter system having alarm, diagnostic and control outputs.

FIG. 1 illustrates a physiological parameter system 100, which may comprise an expert system, a neural-network or a logic circuit, for example. The physiological parameter system 100 has as inputs 101 one or more parameters from one or more physiological measurement devices, such as a pulse oximetry 110 and/or a capnometer 120. Pulse oximeter parameters may include oxygen saturation ($SpO_2$), perfusion index (PI), pulse rate (PR), various signal quality and/or data confidence indicators (Qn) and trend data, to name a few. Capnography parameter inputs may include, for example, an exhaled carbon dioxide waveform, end tidal carbon dioxide ($ETCO_2$) and respiration rate (RR). Signal quality and data confidence indicators are described in U.S. Pat. No. 6,684,090 cited above. The physiological parameter system 100 may also have parameter limits 105, which may be user inputs, default conditions or otherwise predetermined thresholds within the system 100.

The inputs 101 are processed in combination to generate one or more outputs 102 comprising alarms, diagnostics and controls. Alarms may be used to alert medical personnel to a deteriorating condition in a patient under their care. Diagnostics may be used to assist medical personnel in determining a patient condition. Controls may be used to affect the operation of a medical-related device. Other measurement parameters 130 that can be input to the monitor may include or relate to one or more of ECG, blood glucose, blood pressure (BP), temperature (T), HbCO and MetHb, to name a few.

Figure 2:
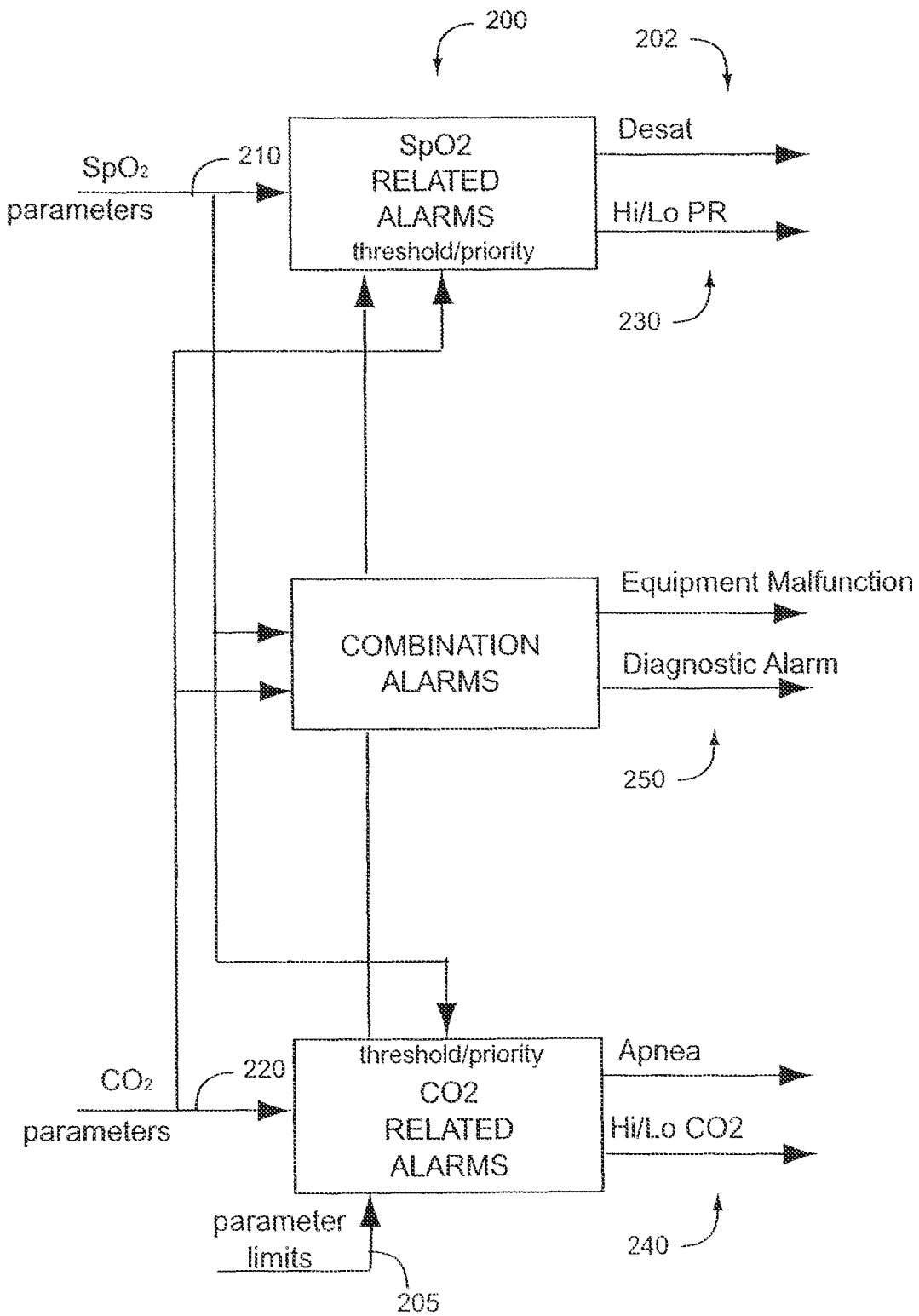
FIG. 2 is a block diagram of a physiological parameter system combining pulse oximetry and capnography and providing alarm outputs.

FIG. 2 illustrates one embodiment of a physiological parameter system 200 combining pulse oximetry parameter inputs 210 and capnography parameter inputs 220 so as to generate alarm outputs 202. Parameter limits 205 may be user inputs, default conditions or otherwise predetermined alarm thresholds for these parameters 210, 220. The alarms 202 are grouped as pulse oximetry related 230, capnography related 240 and a combination 250. For example, a pulse oximetry alarm 230 may be related to percent oxygen saturation and trigger when oxygen saturation falls below a predetermined percentage limit. A capnography alarm 240 may be related to $ETCO_2$ and trigger when $ETCO_2$ falls below or rises above a predetermined mm Hg pressure limit. A combination alarm 250 may indicate a particular medical condition related to both pulse oximetry and capnography or may indicate a malfunction in either instrument.

Figure 3:
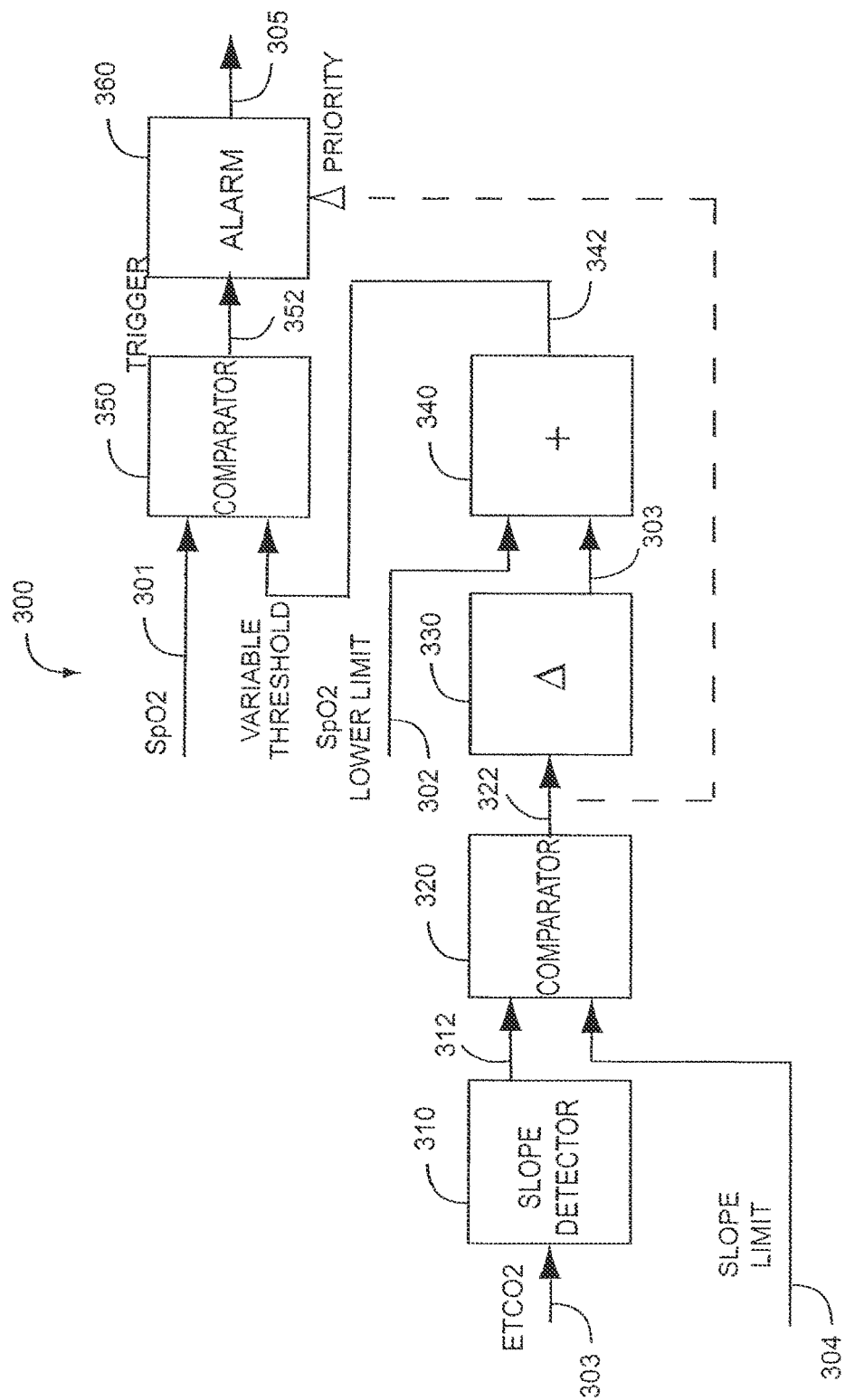
FIG. 3 is a block diagram of a saturation limit alarm enhanced by $ETCO_2$ measurements.

FIG. 3 illustrates a $SpO_2$ alarm embodiment 300 that is responsive to $ETCO_2$. In particular, a $SpO_2$ alarm 305 may be triggered sooner and may indicate a high priority if $ETCO_2$ 303 is falling. That is, if $ETCO_2$ 303 is trending down above a certain rate, the $SpO_2$ alarm 305 is triggered at a higher percentage oxygen saturation threshold and alerts a caregiver to the possibility of a serious condition, e.g., a pulmonary embolism.

As shown in FIG. 3, a slope detector 310 determines the slope 312 of the $ETCO_2$ input 303. A slope comparator 320 compares this slope 312 to a predetermined slope limit 304. If the downward trend of $ETCO_2$ 303 is great enough, a delta value 303 is added 340 to the $SpO_2$ lower limit 302 to generate a variable threshold 342. A threshold comparator 350 compares this variable threshold 342 to the $SpO_2$ input 301 to generate a trigger 352 for the $SpO_2$ alarm 305. The alarm volume, modulation or tone may be altered to indicate priority, based upon the slope comparator output 322.

Figure 4:
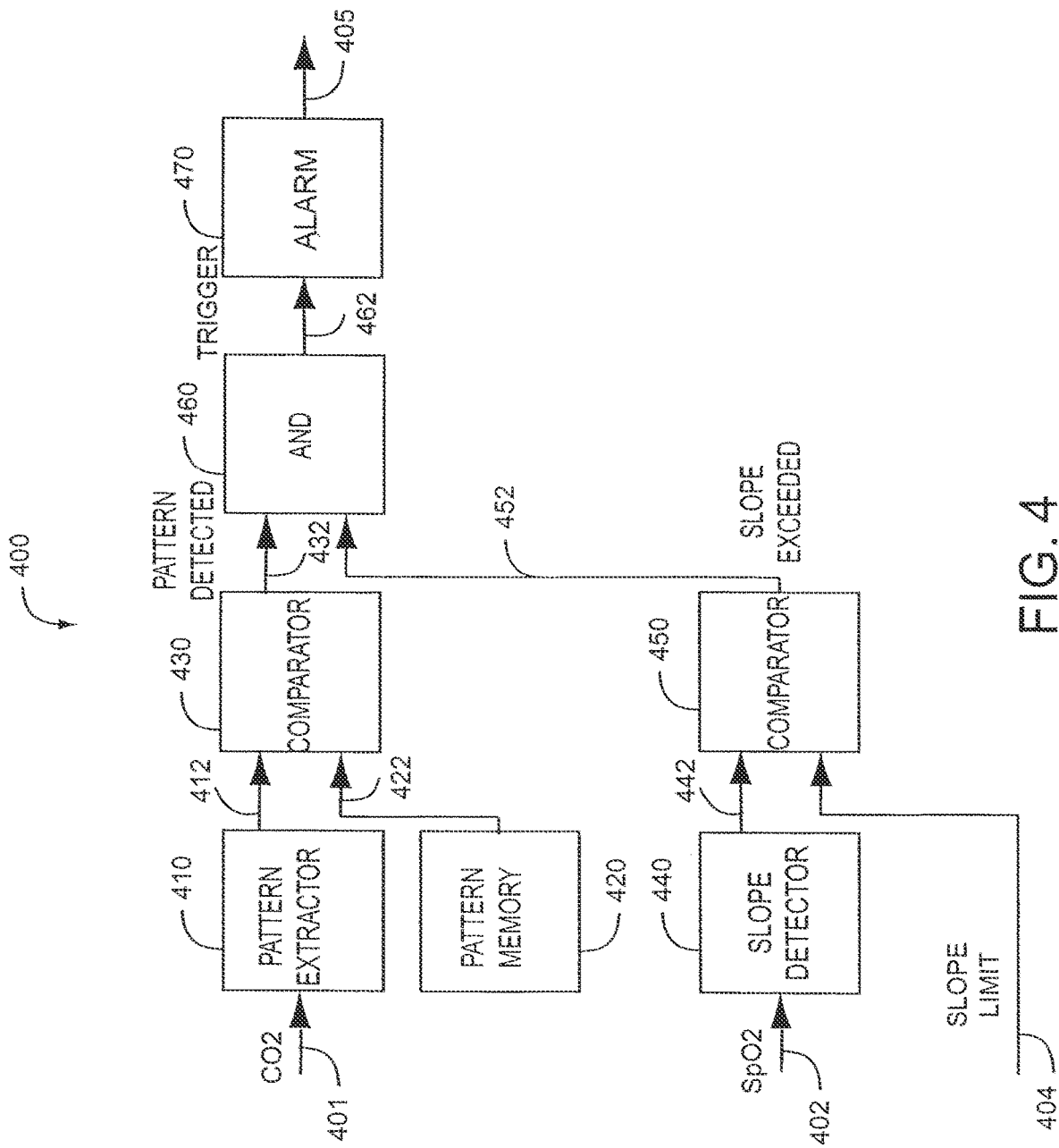
FIG. 4 is a block diagram of a $CO_2$ waveform alarm enhanced by $SpO_2$ measurements.

FIG. 4 illustrates a $CO_2$ alarm embodiment 400 that is responsive to $SpO_2$. In particular, morphology of the input $CO_2$ waveform 401 is utilized to trigger an alarm 405, and that alarm is also responsive to a falling $SpO_2$ 402. That is, if a pattern in the expired $CO_2$ waveform is detected and $SpO_2$ is trending down above a certain rate, then an alarm is triggered. For example, an increasing slope of the $CO_2$ plateau in combination with a downward trend of $SpO_2$ may trigger an alarm and alert a caregiver to the possibility of an airway obstruction.

As shown in FIG. 4, a pattern extractor 410 identifies salient features in the $CO_2$ waveform and generates a corresponding feature output 412. A pattern memory 420 stores one or more sets of predetermined waveform features to detect in the $CO_2$ input 401. The pattern memory 420 is accessed to provide a feature template 422. A feature comparator 430 compares the feature output 412 with the feature template 422 and generates a match output 432 indicating that a specific shape or pattern has been detected in the $CO_2$ waveform 401. In addition, a slope detector 400 determines the slope 442 of the $SpO_2$ input 402. A slope comparator 450 compares this slope 442 to a predetermined slope limit 404. If the downward trend of $SpO_2$ 402 is great enough, a slope exceeded output 452 is generated. If both the match output 432 and the slope exceeded output 452 are each asserted or "true," then a logical AND 460 generates a trigger output 462 to the alarm 470, which generates an alarm output 405.

Figure 5:
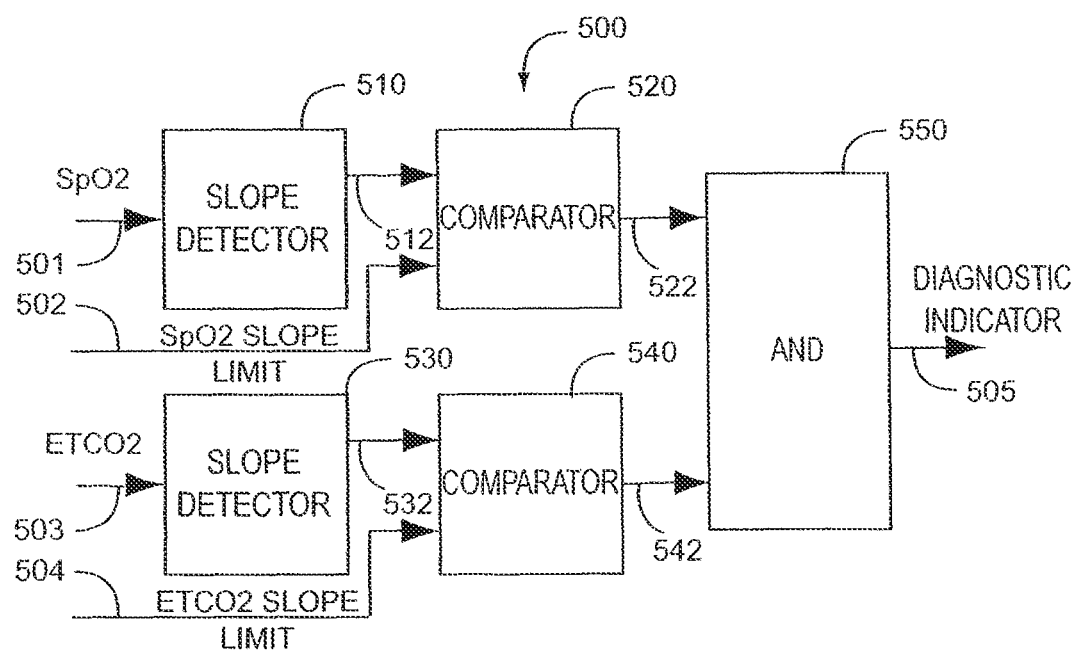
FIG. 5 is a block diagram of a physiological parameter system combining pulse oximetry and capnography and providing a diagnostic output.

FIG. 5 illustrates a combination embodiment 500 having a diagnostic output 505 responsive to both $SpO_2$ 501 and $ETCO_2$ 503 inputs. A $SpO_2$ slope detector 510 determines the slope 512 of the $SpO_2$ input 501 and can be made responsive to a negative slope, a positive slope or s slope absolute value. A first comparator 520 compares this slope 512 to a predetermined $SpO_2$ slope limit 502. If the trend of $SpO_2$ 501 is great enough, a $SpO_2$ slope exceeded output 522 is asserted. Likewise, an $ETCO_2$ slope detector 530 determines the slope 532 of the $ETCO_2$ input 503. A second comparator 540 compares this slope 532 to a predetermined $ETCO_2$ slope limit 504. If the downward trend of $ETCO_2$ 501 is great enough, an $ETCO_2$ slope exceeded output 542 is asserted. If both slope exceeded outputs 522, 542 are asserted or "true," a diagnostic output 505 is asserted.

In one embodiment, the slope detectors 510, 530 are responsive to a negative trend in the $SpO_2$ 501 and $ETCO_2$ 503 inputs, respectively. Accordingly, the diagnostic output 505 indicates a potential embolism or cardiac arrest. In another embodiment, the $SpO_2$ slope detector 510 is responsive to negative trends in the $SpO_2$ 501 input, and the $ETCO_2$ slope detector 530 is responsive to a positive trend in the $ETCO_2$ 503 input. Accordingly, the diagnostic output 505 indicates a potential airway obstruction. The diagnostic output 505 can trigger an alarm, initiate a display, or signal a nursing station, to name a few.

Figure 6A:
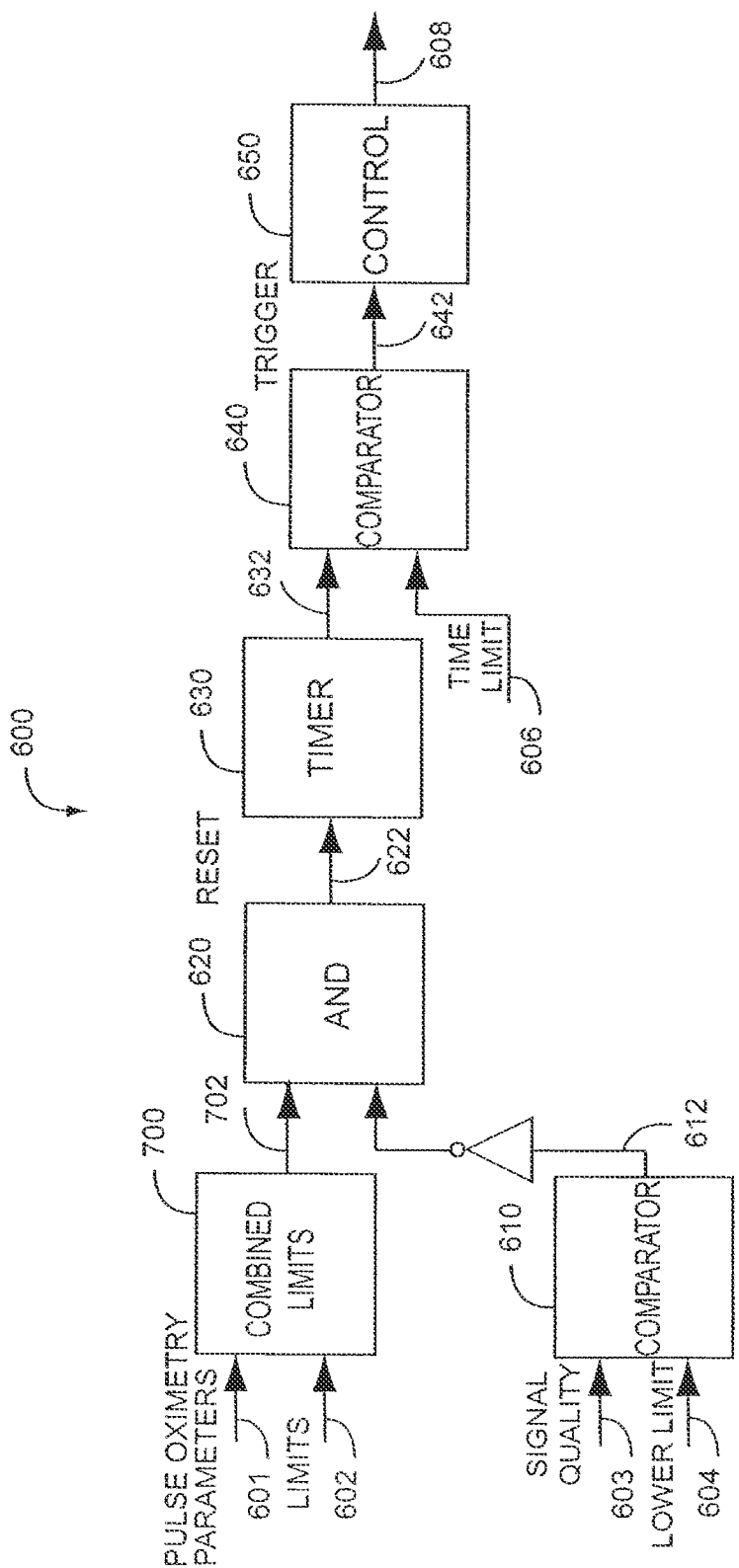
FIGS. 6-7 are block diagrams of a physiological parameter system utilizing pulse oximetry to control patient controlled analgesia (PCA).
Figure 6B:
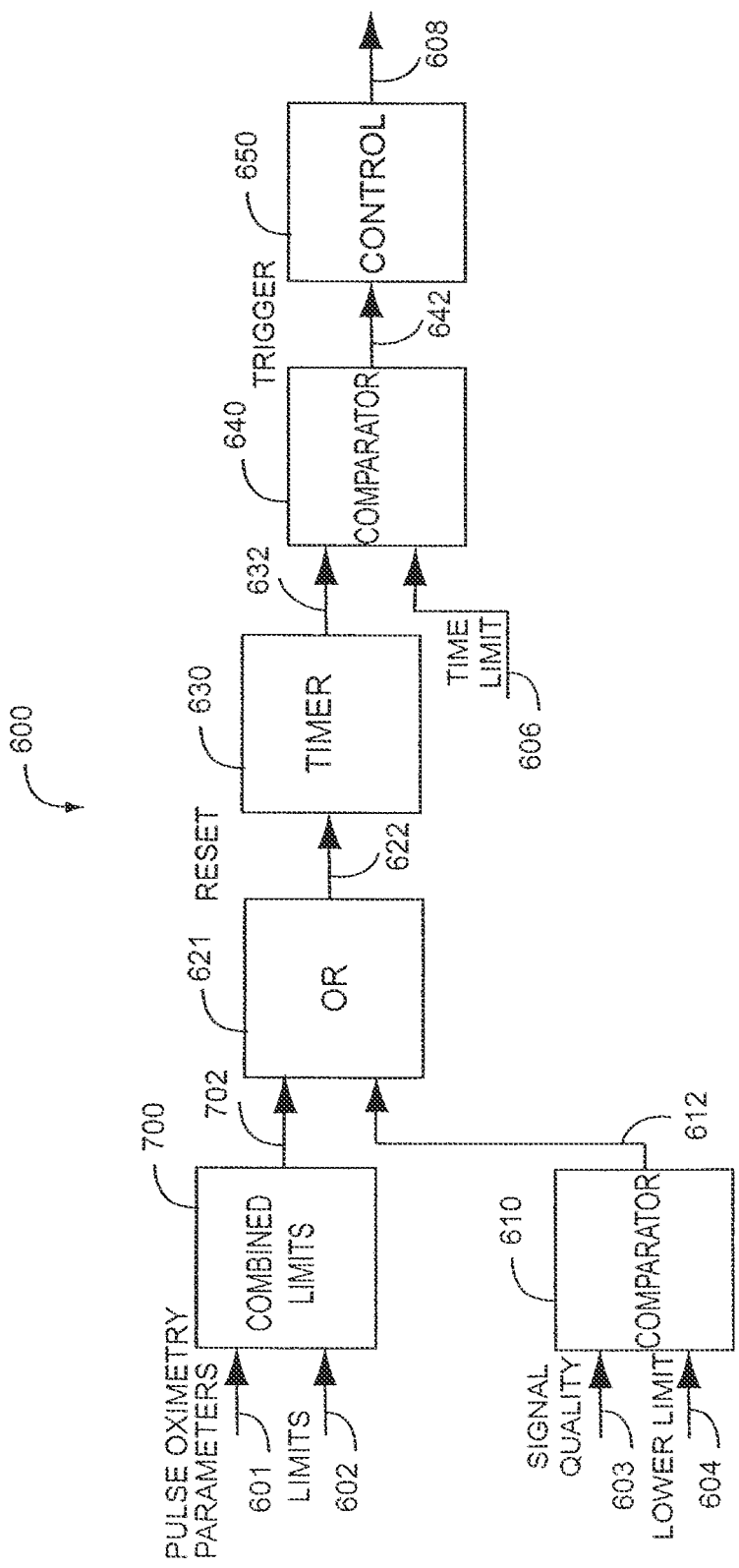

FIGS. 6A-B illustrate a physiological parameter system 600 utilizing pulse oximetry to control patient controlled analgesia (PCA). In particular embodiments, a control output 608 is responsive to pulse oximetry parameters 601 only if signal quality 603 is above a predetermined threshold 604. In FIG. 6A, the control output 608 can be used to lock-out patient controlled analgesia (PCA) if pulse oximetry parameter limits have been exceeded. If signal quality is so low that those parameters are unreliable, however, PCA is advantageously allowed. That is, the pulse oximetry parameters are not allowed to lock-out PCA if those parameters are unreliable. By contrast, in FIG. 6B, the control output 608 can be used to advantageously lock-out or disable patient controlled analgesia (PCA) if pulse oximetry parameter limits have been exceeded or if signal quality is so low that those parameters are unreliable.

As shown in FIG. 6A, pulse oximetry parameters 601 and corresponding limits 602 for those parameters are one set of inputs and a signal quality measures 603 and a corresponding lower limit 604 for signal quality are another set of inputs. The parameters 601 and corresponding limits 602 generate a combined output 703 that is asserted if any of the pulse oximetry parameter limits are exceeded. A comparator 610 compares the signal quality 603 input with a lower limit 604 generating a quality output 612 that is asserted if the signal quality 603 drops below that limit 604. An AND logic 620 generates a reset 622 if the combined output 702 is asserted and the quality output 612 is not asserted. The reset 622 resets the timer 630 to zero. A comparator 640 compares the timer output 632 to a predetermined time limit 606 and generates a trigger 642 if the time limit is exceeded. The trigger 642 causes the control 650 to generate the control output 608, enabling a patient controlled analgesia (PCA), for example. In this manner, the PCA is enabled if all monitored parameters are within set limits and signal quality is above its lower limit for a predetermined period of time.

As shown in FIG. 6B, the combined output 702, quality output 612, reset 622, timer 630, comparator 640 and control 650 are generated as described with respect to FIG. 6A, above. An OR logic 621 generates a rest 622 if either the combined output 702 or the quality output 612 is asserted. In this manner, the PCA is disabled for a predetermined period of time if any of the monitored parameters are outside of set limits or the signal quality is below its lower limit.

Figure 7:
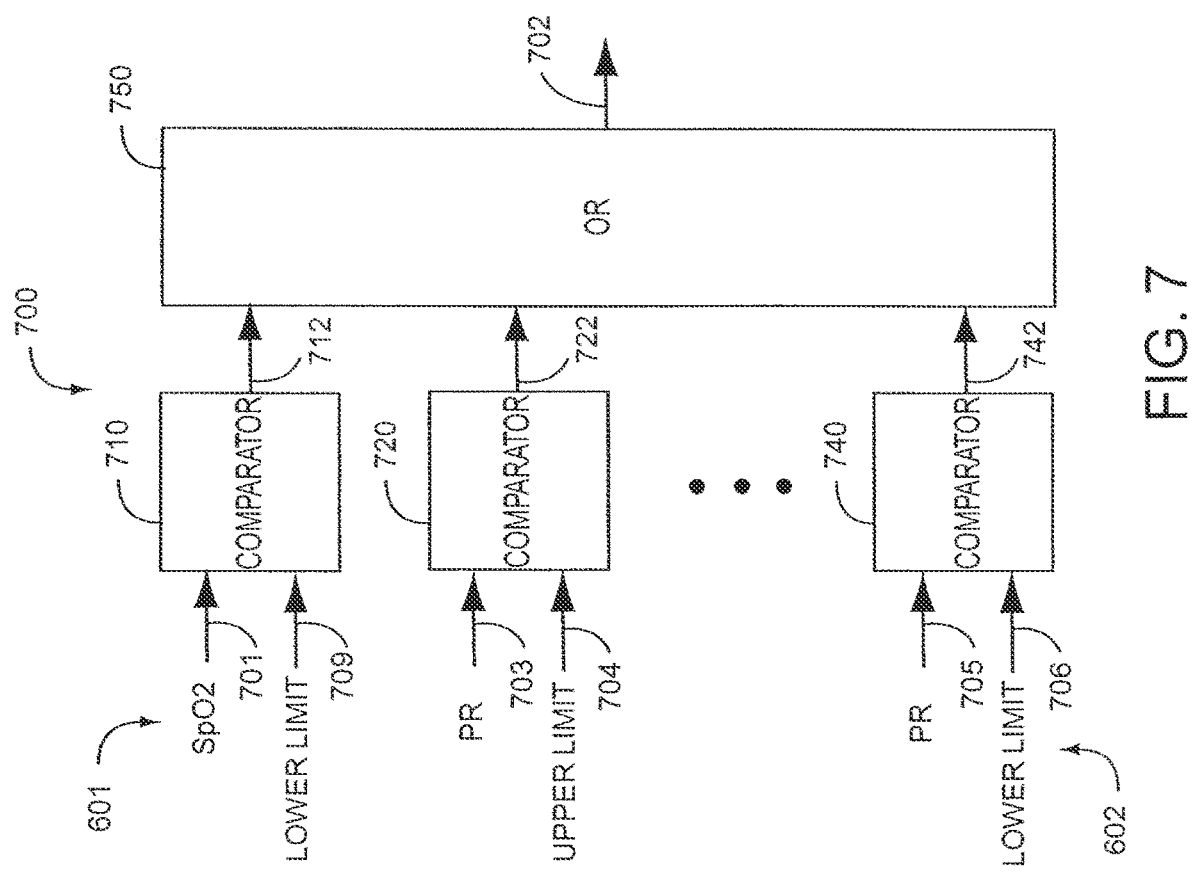

FIG. 7 illustrates combined limits 700 having $SpO_2$ parameters 601 and corresponding thresholds 602 as inputs and providing a combination output 702. In particular, if any parameter 601 exceeds its corresponding limit 602, the output of the corresponding comparator 710, 720, 740 is asserted. An OR logic 750 is responsive to any asserted output 712, 722, 742 to asserted the combined output 702. For example, the combined output 702 may be asserted if $SpO_2$ 701 falls below a lower limit 709, pulse rate (PR) 703 rises above an upper limit 704 or PR 703 falls below a lower limit 706.

A physiological parameter system has been disclosed in detail in connection with various embodiments. These embodiments are disclosed by way of examples only and are not to limit the scope of the claims that follow. One of ordinary skill in the art will appreciate many variations and modifications. For example, the control output 608 (FIG. 6B) can be used to control (titrate) delivered, inspired oxygen levels to patients based upon pulse oximetry parameters, unless signal quality is so low that those parameters are unreliable. One of ordinary skill in the art will also recognize that the control output 608 (FIG. 6B) can be used to control patient delivery of any of various pharmacological agents and/or medical gases.

What is claimed is:

1. A physiological monitor responsive to medical data received from independent medical devices, the physiological monitor comprising one or more hardware processors configured to:
   receive an oxygen saturation measurement responsive to irradiation of a tissue site with an optical sensor, wherein said oxygen saturation measurement has a first alarm threshold;
   receive a secondary parameter responsive to measurement from a second sensor that is different from the optical sensor;
   increase the first alarm threshold for the oxygen saturation measurement based on the received secondary parameter; and
   generate an alarm based on the received oxygen saturation measurement and the increased first alarm threshold.

2. The physiological monitor of claim 1, wherein the secondary parameter is $ETCO_2$.

3. The physiological monitor of claim 1, wherein the secondary parameter is respiration rate.

4. The physiological monitor of claim 1, wherein the secondary parameter is blood pressure.

5. The physiological monitor of claim 1, wherein the second sensor is a capnometer.

6. The physiological monitor of claim 1, wherein the secondary parameter is temperature.

7. The physiological monitor of claim 1, wherein the one or more hardware processors are further configured to control a medical device based on the generated alarm.

8. A physiological monitoring method responsive to medical data received from independent medical devices, the physiological monitoring method comprising:
   receiving an oxygen saturation measurement responsive to irradiation of a tissue site with an optical sensor, wherein said oxygen saturation measurement has a first alarm threshold;
   receiving a secondary parameter responsive to measurement from a second sensor that is different from the optical sensor;
   increasing the first alarm threshold for the oxygen saturation measurement based on the received secondary parameter; and
   generating an alarm based on the received oxygen saturation measurement and the increased first alarm threshold.

9. The physiological monitoring method of claim 8, wherein the secondary parameter is $ETCO_2$.

10. The physiological monitoring method of claim 8, wherein the secondary parameter is respiration rate.

11. The physiological monitoring method of claim 8, wherein the secondary parameter is blood pressure.

12. The physiological monitoring method of claim 8, wherein the second sensor is a capnometer.

13. The physiological monitoring method of claim 8, wherein the secondary parameter is temperature.

14. The physiological monitoring method of claim 8, further comprising controlling a medical device based on the generated alarm.

* * * * *